(12) United States Patent
Govari et al.

(10) Patent No.: US 8,357,152 B2
(45) Date of Patent: Jan. 22, 2013

(54) CATHETER WITH PRESSURE SENSING

(75) Inventors: Assaf Govari, Haifa (IL); Andres Claudio Altmann, Haifa (IL); Yaron Ephrath, Karkur (IL); Yitzhack Schwartz, Haifa (IL)

(73) Assignee: Biosense Webster (Israel), Ltd., Yokneam (IL)

( * ) Notice: Subject to any disclaimer, the term of this patent is extended or adjusted under 35 U.S.C. 154(b) by 1210 days.

(21) Appl. No.: 11/868,733

(22) Filed: Oct. 8, 2007

(65) Prior Publication Data

US 2009/0093806 A1  Apr. 9, 2009

(51) Int. Cl.
*A61B 18/14* (2006.01)
*A61B 5/05* (2006.01)

(52) U.S. Cl. ............. 606/41; 600/424; 600/145; 600/12

(58) Field of Classification Search ............... 606/27–29, 606/33, 34, 41; 600/15, 37, 409, 424, 466, 600/547; 607/101–102; 128/898
See application file for complete search history.

(56) References Cited

U.S. PATENT DOCUMENTS

| | | | |
|---|---|---|---|
| 3,971,364 A | 7/1976 | Fletcher |
| 4,856,993 A | 8/1989 | Maness |
| 5,263,493 A | 11/1993 | Avitall |
| 5,391,199 A | 2/1995 | Ben-Haim |
| 5,499,542 A | 3/1996 | Morlan |
| 5,563,354 A | 10/1996 | Kropp |
| 5,662,124 A | 9/1997 | Wilk |
| 5,680,860 A | 10/1997 | Imran |
| 5,769,843 A | 6/1998 | Abela |
| 5,836,894 A | 11/1998 | Sarvazyan |
| 5,944,022 A | 8/1999 | Nardella |
| 5,964,757 A | 10/1999 | Ponzi |
| 5,974,320 A | 10/1999 | Ward |
| 5,983,126 A | 11/1999 | Wittkampf |
| 6,063,022 A | 5/2000 | Ben Haim |
| 6,123,699 A | 9/2000 | Webster, Jr. |
| 6,171,277 B1 | 1/2001 | Ponzi |
| 6,183,463 B1 | 2/2001 | Webster, Jr. |
| 6,198,974 B1 | 3/2001 | Webster, Jr. |

(Continued)

FOREIGN PATENT DOCUMENTS

| | | |
|---|---|---|
| DE | 19750441 | 6/1999 |
| EP | 1502555 | 2/2005 |

(Continued)

OTHER PUBLICATIONS

Partial European Search Report EP08 25 3265 dated Jan. 15, 2009.

(Continued)

*Primary Examiner* — Lee S Cohen
*Assistant Examiner* — Khadijeh Vahdat
(74) *Attorney, Agent, or Firm* — William A. Schoneman

(57) ABSTRACT

A medical probe includes a flexible insertion tube, having a distal end for insertion into a body cavity of a patient, and a distal tip, which is disposed at the distal end of the insertion tube and is configured to be brought into contact with tissue in the body cavity. A resilient member couples the distal tip to the distal end of the insertion tube and is configured to deform in response to pressure exerted on the distal tip when the distal tip engages the tissue. A position sensor within the probe senses a position of the distal tip relative to the distal end of the insertion tube, which changes in response to deformation of the resilient member.

37 Claims, 2 Drawing Sheets

U.S. PATENT DOCUMENTS

| | | | |
|---|---|---|---|
| 6,216,027 B1 | 4/2001 | Willis et al. | |
| 6,226,542 B1 | 5/2001 | Reisfeld | |
| 6,239,724 B1 | 5/2001 | Doron et al. | |
| 6,241,724 B1 | 6/2001 | Fleischman et al. | |
| 6,272,371 B1 | 8/2001 | Shlomo | |
| 6,272,672 B1 | 8/2001 | Conway | |
| 6,301,496 B1 | 10/2001 | Reisfeld | |
| 6,332,089 B1 | 12/2001 | Acker et al. | |
| 6,335,617 B1 | 1/2002 | Osadchy | |
| 6,436,059 B1 | 8/2002 | Zanelli | |
| 6,456,864 B1 | 9/2002 | Swanson | |
| 6,484,118 B1 | 11/2002 | Govari | |
| 6,551,302 B1 | 4/2003 | Rosinko | |
| 6,574,492 B1 | 6/2003 | Ben Haim | |
| 6,584,856 B1 | 7/2003 | Biter | |
| 6,612,992 B1 | 9/2003 | Hossack | |
| 6,618,612 B1 | 9/2003 | Acker et al. | |
| 6,690,963 B2 | 2/2004 | Ben-Haim et al. | |
| 6,695,808 B2 | 2/2004 | Tom | |
| 6,814,733 B2 | 11/2004 | Schwartz | |
| 6,892,091 B1* | 5/2005 | Ben-Haim et al. | 600/509 |
| 6,915,149 B2 | 7/2005 | Ben-Haim | |
| 6,964,205 B2 | 11/2005 | Papakostas | |
| 6,973,339 B2 | 12/2005 | Govari | |
| 6,997,924 B2 | 2/2006 | Schwartz | |
| 7,077,823 B2 | 7/2006 | McDaniel | |
| 7,156,816 B2 | 1/2007 | Schwartz | |
| 7,306,593 B2 | 12/2007 | Keidar | |
| 7,311,704 B2 | 12/2007 | Paul et al. | |
| 7,536,218 B2 | 5/2009 | Govari | |
| 7,681,432 B2 | 3/2010 | Hay | |
| 7,686,767 B2 | 3/2010 | Maschke | |
| 2001/0047129 A1 | 11/2001 | Hall | |
| 2001/0047133 A1* | 11/2001 | Gilboa et al. | 600/429 |
| 2002/0065455 A1 | 5/2002 | Ben-Haim et al. | |
| 2002/0068866 A1 | 6/2002 | Zikorus et al. | |
| 2002/0165461 A1 | 11/2002 | Hayzelden | |
| 2003/0120150 A1 | 6/2003 | Govari | |
| 2003/0120195 A1 | 6/2003 | Milo | |
| 2003/0130615 A1 | 7/2003 | Tom | |
| 2003/0158494 A1 | 8/2003 | Dahl | |
| 2004/0049255 A1 | 3/2004 | Jain | |
| 2004/0064024 A1 | 4/2004 | Sommer | |
| 2004/0068178 A1 | 4/2004 | Govari | |
| 2004/0102769 A1 | 5/2004 | Schwartz | |
| 2004/0147920 A1 | 7/2004 | Keidar | |
| 2004/0254458 A1 | 12/2004 | Govari | |
| 2005/0033135 A1 | 2/2005 | Govari | |
| 2005/0080429 A1 | 4/2005 | Freyman | |
| 2005/0277875 A1 | 12/2005 | Selkee | |
| 2006/0009690 A1 | 1/2006 | Fuimaono | |
| 2006/0009735 A1 | 1/2006 | Viswanathan | |
| 2006/0015096 A1 | 1/2006 | Hauck | |
| 2006/0173480 A1 | 8/2006 | Zhang | |
| 2006/0200049 A1 | 9/2006 | Leo et al. | |
| 2006/0247618 A1* | 11/2006 | Kaplan et al. | 606/41 |
| 2007/0021742 A1 | 1/2007 | Viswanathan | |
| 2007/0060832 A1 | 3/2007 | Levin | |
| 2007/0100332 A1 | 5/2007 | Paul et al. | |
| 2007/0106114 A1* | 5/2007 | Sugimoto et al. | 600/117 |
| 2007/0179492 A1 | 8/2007 | Pappone | |
| 2007/0191829 A1* | 8/2007 | McGee et al. | 606/41 |
| 2008/0009750 A1 | 1/2008 | Aeby et al. | |
| 2008/0015568 A1 | 1/2008 | Paul | |
| 2008/0051704 A1 | 2/2008 | Patel | |
| 2008/0077049 A1 | 3/2008 | Hirshman | |
| 2008/0183075 A1 | 7/2008 | Govari | |
| 2008/0249522 A1 | 10/2008 | Pappone | |
| 2008/0255540 A1 | 10/2008 | Selkee | |
| 2008/0275428 A1 | 11/2008 | Tegg et al. | |
| 2008/0275442 A1 | 11/2008 | Paul et al. | |
| 2008/0275465 A1 | 11/2008 | Paul | |
| 2008/0281319 A1 | 11/2008 | Paul | |
| 2008/0287777 A1 | 11/2008 | Li | |
| 2008/0288038 A1 | 11/2008 | Paul | |
| 2008/0294144 A1 | 11/2008 | Leo | |
| 2008/0294158 A1 | 11/2008 | Pappone | |
| 2009/0010021 A1 | 1/2009 | Smith | |
| 2009/0093806 A1 | 4/2009 | Govari et al. | |
| 2009/0138007 A1 | 5/2009 | Govari | |
| 2009/0158511 A1 | 6/2009 | Maze | |
| 2009/0287118 A1 | 11/2009 | Malek | |
| 2009/0306650 A1* | 12/2009 | Govari et al. | 606/41 |
| 2010/0137845 A1 | 6/2010 | Ramstein | |
| 2010/0152574 A1 | 6/2010 | Erdman | |
| 2010/0168620 A1 | 7/2010 | Klimovitch | |
| 2010/0168918 A1 | 7/2010 | Zhao | |
| 2011/0184406 A1 | 7/2011 | Selkee | |
| 2012/0149966 A1* | 6/2012 | Ludwin et al. | 600/11 |
| 2012/0149967 A1* | 6/2012 | Ludwin et al. | 600/11 |
| 2012/0150075 A1* | 6/2012 | Ludwin et al. | 600/587 |

FOREIGN PATENT DOCUMENTS

| | | |
|---|---|---|
| EP | 1 586 281 A | 10/2005 |
| EP | 1690564 | 8/2006 |
| EP | 1 743 575 A2 | 1/2007 |
| EP | 0928601 B1 | 4/2007 |
| EP | 1897581 | 8/2007 |
| EP | 2047797 | 3/2008 |
| EP | 2 000 789 A2 | 12/2008 |
| EP | 2000789 A2 | 12/2008 |
| EP | 1586281 B1 | 4/2009 |
| EP | 1820464 | 4/2009 |
| EP | 2047797 A3 | 4/2009 |
| EP | 2130508 A | 9/2009 |
| EP | 2338411 | 9/2009 |
| EP | 2338412 | 12/2009 |
| EP | 2130508 B1 | 12/2011 |
| JP | 2005345215 | 4/2010 |
| JP | 2006064465 | 6/2011 |
| WO | WO95/10326 | 4/1995 |
| WO | WO 96/05768 A1 | 2/1996 |
| WO | WO97/29678 | 8/1997 |
| WO | WO97/29709 A1 | 8/1997 |
| WO | WO97/29710 A1 | 8/1997 |
| WO | WO 98/29032 A | 7/1998 |
| WO | WO98/29032 A1 | 7/1998 |
| WO | WO03/020139 | 3/2003 |
| WO | WO2006/029563 | 3/2006 |
| WO | WO2006/086152 | 8/2006 |
| WO | WO2006/092563 | 9/2006 |
| WO | WO2007/025230 | 3/2007 |
| WO | WO2007/050960 | 3/2007 |
| WO | WO2007/067938 | 6/2007 |
| WO | WO2007/082216 | 7/2007 |
| WO | WO2007/098494 | 8/2007 |
| WO | WO 2007/111182 | 10/2007 |
| WO | WO2009/015868 | 6/2008 |
| WO | WO2009/085470 | 7/2009 |
| WO | WO2009/147399 | 12/2009 |
| WO | WO20010/000897 | 1/2010 |

OTHER PUBLICATIONS

EP Partial Search Report No. EP 08 25 3265 dated Jan. 15, 2009.
EP Partial Search Report No. EP 08 25 3265 dated Aug. 19, 2009.
Okumura, Y. et al. A Systematic Analysis of in Vivo Contact Forces on Virtual Catheter Tip-Tissue Surface Contact During Cardiac Mapping and Intervention. J of Cardiovasc Electrophysiol, vol. 19, pp. 632-640, Jun. 2008.

* cited by examiner

CATHETER WITH PRESSURE SENSING

FIELD OF THE INVENTION

The present invention relates generally to invasive medical devices, and specifically to methods and devices for sensing pressure exerted against a probe, such as a catheter, inside the body of a patient.

BACKGROUND OF THE INVENTION

Intracardiac radio-frequency (RF) ablation is a well-known method for treating cardiac arrhythmias. Typically, a catheter having an electrode at its distal tip is inserted through the patient's vascular system into a chamber of the heart. The electrode is brought into contact with a site (or sites) on the endocardium, and RF energy is applied through the catheter to the electrode in order to ablate the heart tissue at the site. It is important to ensure proper contact between the electrode and the endocardium during ablation in order to achieve the desired therapeutic effect without excessive damage to the tissue.

Various techniques have been suggested for verifying electrode contact with the tissue. For example, U.S. Pat. No. 6,695,808, whose disclosure is incorporated herein by reference, describes apparatus for treating a selected patient tissue or organ region. A probe has a contact surface that may be urged against the region, thereby creating contact pressure. A pressure transducer measures the contact pressure. This arrangement is said to meet the needs of procedures in which a medical instrument must be placed in firm but not excessive contact with an anatomical surface, by providing information to the user of the instrument that is indicative of the existence and magnitude of the contact force.

As another example, U.S. Pat. No. 6,241,724, whose disclosure is incorporated herein by reference, describes methods for creating lesions in body tissue using segmented electrode assemblies. In one embodiment, an electrode assembly on a catheter carries pressure transducers, which sense contact with tissue and convey signals to a pressure contact module. The module identifies the electrode elements that are associated with the pressure transducer signals and directs an energy generator to convey RF energy to these elements, and not to other elements that are in contact only with blood.

A further example is presented in U.S. Pat. No. 6,915,149, whose disclosure is incorporated herein by reference. This patent describes a method for mapping a heart using a catheter having a tip electrode for measuring the local electrical activity. In order to avoid artifacts that may arise from poor tip contact with the tissue, the contact pressure between the tip and the tissue is measured using a pressure sensor to ensure stable contact.

U.S. Patent Application Publication 2007/0100332, whose disclosure is incorporated herein by reference, describes systems and methods for assessing electrode-tissue contact for tissue ablation. An electro-mechanical sensor within the catheter shaft generates electrical signals corresponding to the amount of movement of the electrode within a distal portion of the catheter shaft. An output device receives the electrical signals for assessing a level of contact between the electrode and a tissue.

SUMMARY OF THE INVENTION

The embodiments of the present invention that are described hereinbelow provide a novel design of an invasive probe, such as a catheter, as well as systems and methods making use of such a probe. The design is particularly useful in achieving and verifying proper contact between the distal tip of the probe and tissue that the probe engages inside the body.

In some embodiments, the probe comprises a flexible insertion tube, having a distal end for insertion into a body cavity of a patient. The distal tip of the probe is coupled to the distal end of the insertion tube by a resilient member, such as a spring, which deforms in response to pressure exerted on the distal tip when it engages the tissue. A position sensor within the probe senses the position of the distal tip relative to the distal end of the insertion tube, which is indicative of deformation of the resilient member, and is thus able to give an indication of the pressure.

In a disclosed embodiment, the sensor may comprise a magnetic field sensor in the distal tip, and the probe may thus be used as part of a system that determines the coordinates of the distal tip within the body using magnetic fields. For this purpose, a first magnetic field generator, disposed outside the body of the patient, generates a magnetic field within the body. The distal end of the insertion tube contains a second (typically much smaller) magnetic field generator. The sensor in the distal tip generates signals responsively to the magnetic fields of both the first and second field generators. These signals are processed both to determine coordinates of the distal tip within the body and to detect changes in the position of the distal tip relative to the distal end of the insertion tube, which are indicative of deformation of the resilient member and hence of the pressure exerted on the distal tip.

Alternatively, the distal tip may contain a magnetic field generator, and the field that it generates may be measured by sensors in the distal end of the insertion tube and outside the body for the purposes of detection of sensing pressure on and position coordinates of the distal tip.

There is therefore provided, in accordance with an embodiment of the present invention, a medical probe, including:

a flexible insertion tube, having a distal end for insertion into a body cavity of a patient;

a distal tip, which is disposed at the distal end of the insertion tube and is configured to be brought into contact with tissue in the body cavity;

a resilient member, which couples the distal tip to the distal end of the insertion tube and is configured to deform in response to pressure exerted on the distal tip when the distal tip engages the tissue; and a position sensor within the probe for sensing a position of the distal tip relative to the distal end of the insertion tube, which changes in response to deformation of the resilient member.

In disclosed embodiments, the position sensor is configured to generate a signal indicative of an axial displacement and an orientation of the distal tip relative to the distal end of the insertion tube. In some embodiments, the position sensor is configured to generate the signal responsively to a magnetic field that is generated in a vicinity of the distal tip. In one embodiment, the position sensor is disposed in the distal end of the insertion tube, and the probe includes a magnetic field generator within the distal tip for generating the magnetic field. In another embodiment, the position sensor is disposed in the distal tip, and the probe includes a magnetic field generator within the distal end of the insertion tube for generating the magnetic field. Typically, the position sensor and the magnetic field generator include coils.

In one embodiment, the resilient member includes a spring, and the position sensor is configured to generate a signal, responsively to the deformation, which is indicative of the pressure exerted on the distal tip.

In a disclosed embodiment, the distal tip includes an electrode, which is configured to make electrical contact with the tissue, wherein the electrode is coupled to apply electrical energy to the tissue so as to ablate a region of the tissue.

There is also provided, in accordance with an embodiment of the present invention, apparatus for performing a medical procedure inside a body of a patient, the apparatus including:

a first magnetic field generator, for disposition outside the body of the patient, for generating a first magnetic field within the body;

a probe, which includes:
an insertion tube having a distal end for insertion into a body cavity of a patient;
a second magnetic field generator within the distal end of the insertion tube for generating a second magnetic field;
a distal tip, which is flexibly coupled to the distal end of the insertion tube; and
a sensor, which is disposed within the distal tip and is configured to generate first and second signals responsively to the first and second magnetic fields, respectively; and a processor, which is coupled to receive and process the first signal so as to determine coordinates of the distal tip within the body and to receive and process the second signal so as to detect changes in a position of the distal tip relative to the distal end of the insertion tube.

In some embodiments, the distal tip is rigid, and the probe includes a resilient member, which couples the distal tip to the distal end of the insertion tube. Typically, the resilient member is configured to deform in response to pressure exerted on the distal tip when the distal tip engages tissue inside the body, and the changes in the position of the distal tip are indicative of deformation of the resilient member, while the processor is configured to generate, responsively to the deformation, an output that is indicative of the pressure exerted on the distal tip. Optionally, the processor may be configured to generate a control input for automatically controlling motion of the probe within the body cavity responsively to the first and second signals.

There is additionally provided, in accordance with an embodiment of the present invention, a method for contacting tissue in a body cavity of a patient, the method including:

inserting a probe into the body cavity, the probe including a flexible insertion tube and a distal tip, which is coupled to a distal end of the insertion tube by a resilient member, and including a position sensor, which generates a signal indicative of a position of the distal tip relative to the distal end of the insertion tube, which changes in response to deformation of the resilient member;

advancing the probe within the body cavity so that the distal tip engages and applies a pressure against the tissue, thereby causing the resilient member to deform; and processing the signal while the distal tip engages the tissue so as to provide an indication of the pressure.

In a disclosed embodiment, advancing the probe includes bringing an electrode on the distal tip into electrical contact with the tissue, and the method includes applying electrical energy to the electrode so as to ablate a region of the tissue that is engaged by the distal tip. Applying the electrical energy may include controlling application of the energy responsively to the indication of the pressure, so that the electrical energy is applied to the electrode when the pressure is within a desired range.

There is further provided, in accordance with an embodiment of the present invention, apparatus for performing a medical procedure inside a body of a patient, the apparatus including:

a probe, which includes:
an insertion tube having a distal end for insertion into a body cavity of a patient;
a distal tip, which is flexibly coupled to the distal end of the insertion tube;
a magnetic field generator, which is disposed within the distal tip and is configured to generate a magnetic field; and
a first sensor within the distal end of the insertion tube for generating a first signal in response to the magnetic field; and a second sensor, for disposition outside the body of the patient, for generating a second signal in response to the magnetic field;

a processor, which is coupled to receive and process the second signal so as to determine coordinates of the distal tip within the body and to receive and process the first signal so as to detect changes in a position of the distal tip relative to the distal end of the insertion tube.

The present invention will be more fully understood from the following detailed description of the embodiments thereof, taken together with the drawings in which:

DETAILED DESCRIPTION OF EMBODIMENTS

Figure 1:
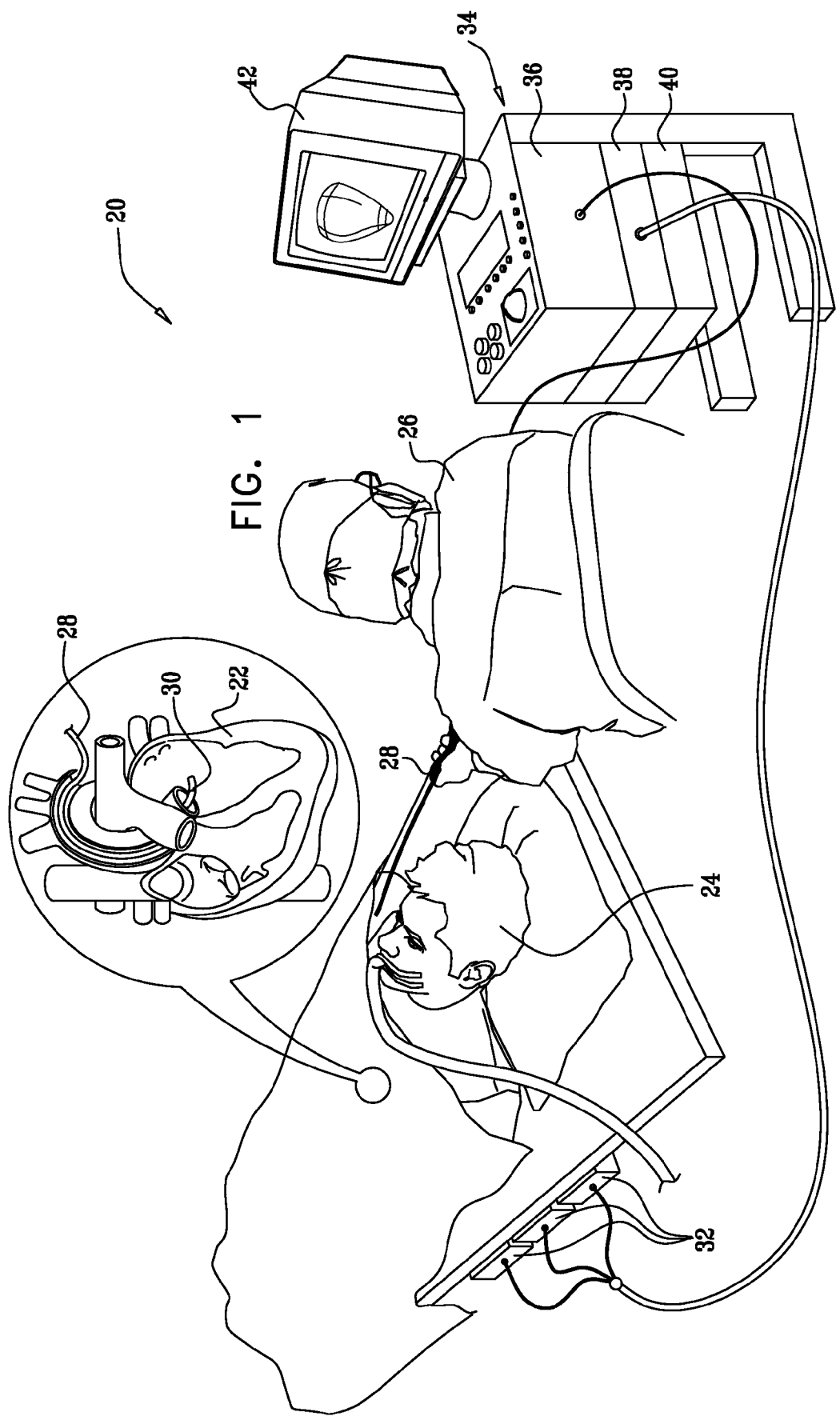
FIG. 1 is a schematic, pictorial illustration of a catheter-based medical system, in accordance with an embodiment of the present invention.

FIG. 1 is a schematic, pictorial illustration of a system 20 for cardiac catheterization, in accordance with an embodiment of the present invention. System 20 may be based, for example, on the CARTO™ system, produced by Biosense Webster Inc. (Diamond Bar, Calif.). This system comprises an invasive probe in the form of a catheter 28 and a control console 34. In the embodiment described hereinbelow, it is assumed that catheter 28 is used in ablating endocardial tissue, as is known in the art. Alternatively, the catheter may be used mutatis mutandis, for other therapeutic and/or diagnostic purposes in the heart or in other body organs.

An operator 26, such as a cardiologist, inserts catheter 28 through the vascular system of a patient 24 so that a distal end 30 of the catheter enters a chamber of the patient's heart 22. The operator advances the catheter so that the distal tip of the catheter engages endocardial tissue at a desired location or locations. Catheter 28 is typically connected by a suitable connector at its proximal end to console 34. The console comprises a radio frequency (RF) generator 40, which supplies high-frequency electrical energy via the catheter for ablating tissue in the heart at the locations engaged by the distal tip, as described further hereinbelow. Alternatively, the catheter and system may be configured to perform ablation by other techniques that are known in the art, such as cryoablation.

Console 34 uses magnetic position sensing to determine position coordinates of distal end 30 inside heart 22. For this purpose, a driver circuit 38 in console 34 drives field generators 32 to generate magnetic fields within the body of patient 24. Typically, the field generators comprise coils, which are placed below the patient's torso at known positions external to the patient. These coils generate magnetic fields in a predefined working volume that contains heart 22. A magnetic field sensor within distal end 30 of catheter 28 (shown in FIG. 2) generates electrical signals in response to these magnetic fields. A signal processor 36 processes these signals in order to determine the position coordinates of the distal end, typically including both location and orientation coordinates. This method of position sensing is implemented in the above-mentioned CARTO system and is described in detail in U.S. Pat. Nos. 5,391,199, 6,690,963, 6,484,118, 6,239,724, 6,618, 612 and 6,332,089, in PCT Patent Publication WO 96/05768, and in U.S. Patent Application Publications 2002/0065455 A1, 2003/0120150 A1 and 2004/0068178 A1, whose disclosures are all incorporated herein by reference.

Processor 36 typically comprises a general-purpose computer, with suitable front end and interface circuits for receiving signals from catheter 28 and controlling the other components of console 34. The processor may be programmed in software to carry out the functions that are described herein. The software may be downloaded to console 34 in electronic form, over a network, for example, or it may be provided on tangible media, such as optical, magnetic or electronic memory media. Alternatively, some or all of the functions of processor 36 may be carried out by dedicated or programmable digital hardware components. Based on the signals received from the catheter and other components of system 20, processor 36 drives a display 42 to give operator 26 visual feedback regarding the position of distal end 30 in the patient's body, as well as status information and guidance regarding the procedure that is in progress.

Alternatively or additionally, system 20 may comprise an automated mechanism for maneuvering and operating catheter 28 within the body of patient 24. Such mechanisms are typically capable of controlling both the longitudinal motion (advance/retract) of the catheter and transverse motion (deflection/steering) of the distal end of the catheter. Some mechanisms of this sort use DC magnetic fields for this purpose, for example. In such embodiments, processor 36 generates a control input for controlling the motion of the catheter based on the signals provided by the magnetic field sensor in the catheter. These signals are indicative of both the position of the distal end of the catheter and of force exerted on the distal end, as explained further hereinbelow.

Figure 2:
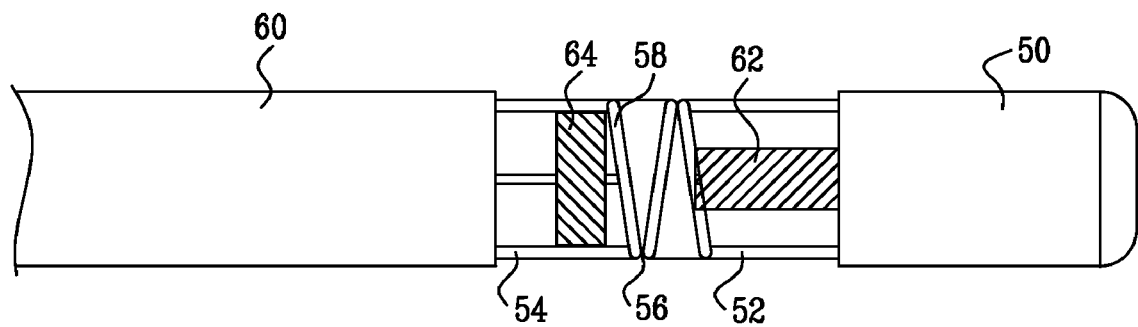
FIG. 2 is a schematic, cutaway view showing details of the distal end of a catheter, in accordance with an embodiment of the present invention.

FIG. 2 is a schematic, cutaway view of distal end 30 of catheter 28, showing details of the structure of the catheter in accordance with an embodiment of the present invention. Catheter 28 comprises a flexible insertion tube 54, with a distal tip 52 connected to the distal end of tube 54 at a joint 56. The insertion tube is covered by a flexible, insulating material 60, such as Celcon® or Teflon®. The area of joint 56 is covered, as well, by a flexible, insulating material, which may be the same as material 60 or may be specially adapted to permit unimpeded bending and compression of the joint, (This material is cut away in FIG. 2 in order to expose the internal structure of the catheter.) Distal tip 52 may be covered, at least in part, by an electrode 50, which is typically made of a metallic material, such as a platinum/iridium alloy. Alternatively, other suitable materials may be used, as will be apparent to those skilled in the art. Further alternatively, the distal tip may be made without a covering electrode. The distal tip is typically relatively rigid, by comparison with the flexible insertion tube.

Distal tip 52 is connected to the distal end of insertion tube 54 by a resilient member 58. In FIG. 2, the resilient member has the form of a coil spring, but other types of resilient components may alternatively be used for this purpose. For example, resilient member 58 may comprise a polymer, such as silicone, polyurethane, or other plastics, with the desired flexibility and strength characteristics. Resilient member 58 permits a limited range of relative movement between tip 52 and insertion tube 54 in response to forces exerted on the distal tip. Such forces are encountered when the distal tip is pressed against the endocardium during an ablation procedure. The desired pressure for good electrical contact between the distal tip and the endocardium during ablation is on the order of 20-30 grams. The spring serving as the resilient member in this embodiment may be configured, for example, to permit axial displacement (i.e., lateral movement along the axis of catheter 28) of the distal tip by about 1-2 mm and angular deflection of the distal tip by up to about 30° relative to the distal end of the insertion tube, in response to the desired pressure.

As noted above, distal tip 52 contains a magnetic position sensor 62. Sensor 62 may comprise one or more miniature coils, and typically comprises multiple coils oriented along different axes. Alternatively, sensor 62 may comprise another type of magnetic sensor, such as a Hall effect or magnetoresistive sensor, for example. The magnetic fields created by field generators 32 cause these coils to generate electrical signals, with amplitudes that are indicative of the position and orientation of sensor 62 relative to the fixed frame of reference of field generators 32. Processor 36 receives these signals via wires (not shown in the figures) running through catheter 28, and processes the signals in order to derive the location and orientation coordinates of distal tip 52 in this fixed frame of reference, as described in the patents and patent applications cited above.

In addition, insertion tube 54 contains a miniature magnetic field generator 64 near the distal end of the insertion tube. Typically, field generator 64 comprises a coil, which is driven by a current conveyed through catheter 28 from console 34. The current is generated so as to create a magnetic field that is distinguishable in time and/or frequency from the fields of field generators 32. For example, the current to field generator 64 may be generated at a selected frequency in the range between about 16 kHz and 25 kHz, while field generators 32 are driven at different frequencies. Additionally or alternatively, the operation of generators 32 and 64 may be time-multiplexed.

The magnetic field created by field generator 64 causes the coils in sensor 62 to generate electrical signals at the drive frequency of field generator 64. The amplitudes of these signals will vary depending upon the location and orientation of distal tip 52 relative to insertion tube 54. Processor 36 processes these signals in order to determine the axial displacement and the magnitude of the angular deflection of the distal tip relative to the insertion tube. (Because of the axial symmetry of the field generated by a coil, only the magnitude of the deflection can be detected using a single coil in field generator 64, and not the direction of the deflection. Optionally, field generator 64 may comprise two or more coils, in which case the direction of deflection may be determined, as well.) The readings of displacement and deflection are typically accurate to within a few tenths of a millimeter and about one degree, respectively. The magnitudes of the displacement and deflection may be combined by vector addition to give a total magnitude of the movement of distal tip 52 relative to the distal end of insertion tube 54.

The relative movement of the distal tip relative to the distal end of the insertion tube gives a measure of the deformation of resilient member 58. Generally speaking, this deformation is proportional to the force that is exerted on the resilient member, which is roughly equal to the force that is exerted on the distal tip by the heart tissue with which the distal tip is in contact. Thus, the combination of field generator 64 with sensor 62 serves as a pressure sensing system, for determining the approximate pressure exerted by the endocardial tissue on the distal tip of the catheter (or equivalently, the pressure exerted by electrode 50 against the endocardial tissue). By virtue of the combined sensing of displacement and deflection, this pressure sensing system reads the pressure correctly regardless of whether the electrode engages the endocardium head-on or at an angle. The pressure reading is insensitive to temperature variations and free of drift, unlike piezoelectric sensors, for example.

Figure 3:
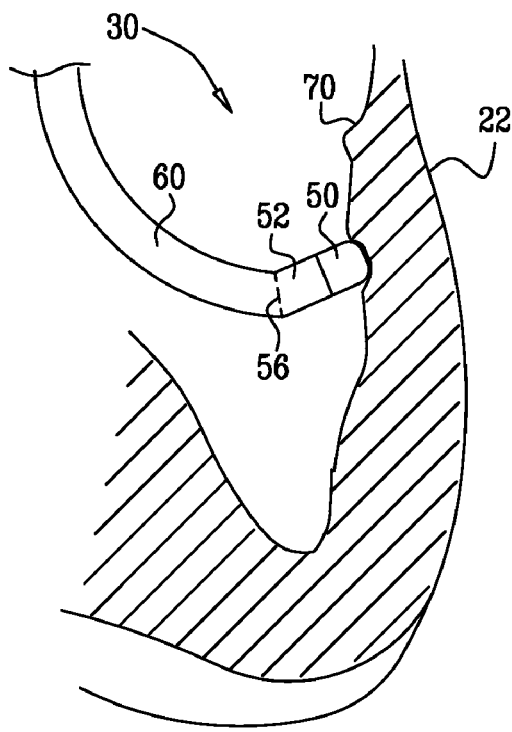
FIG. 3 is a schematic detail view showing the distal tip of a catheter in contact with endocardial tissue, in accordance with an embodiment of the present invention.

FIG. 3 is a schematic detail view showing distal end 30 of catheter 28 in contact with endocardium 70 of heart 22, in accordance with an embodiment of the present invention. Pressure exerted by the distal tip against the endocardium deforms the endocardial tissue slightly, so that electrode 50 contacts the tissue over a relatively large area. Since the electrode engages the endocardium at an angle, rather than head-on, distal tip 52 bends at joint 56 relative to the insertion tube of the catheter. The bend facilitates optimal contact between the electrode and the endocardial tissue.

Processor 36 receives and processes the signals generated by sensor 62 in response to the magnetic field of generator 64, in order to derive an indication of the pressure exerted by distal tip 52 on endocardium 70. As noted earlier, for good ablation, pressure of about 20-30 grams is desirable. Lower pressure means that there may be inadequate contact between electrode 50 and the endocardial tissue. As a result, much or all of the RF energy may be carried away by the blood inside the heart, and the tissue will be ablated inadequately or not at all. Higher pressure means that the electrode is pressing too hard against the endocardial tissue. Excessive pressure of this sort may cause severe cavitation in the tissue, leading to extensive tissue damage and possibly even perforation of the heart wall.

To avoid these eventualities, console 34 outputs an indication of the pressure measured using sensor 62 to operator 26, and may issue an alarm if the pressure is too low or too high. Optionally, RF generator 40 may be interlocked, so as to supply RF power to electrode 50 only when the pressure against the tissue is in the desired range. Alternatively or additionally, the pressure indication may be used in closed-loop control of an automated mechanism for maneuvering and operating catheter 28, as described hereinabove, to ensure that the mechanism causes the distal end of the catheter to engage the endocardium in the proper location and with the appropriate pressure against the tissue.

In an alternative embodiment, the roles of sensor 62 and magnetic field generators 32 and 64 may be reversed. In other words, driver circuit 38 may drive a magnetic field generator in distal tip 52 to generate one or more magnetic fields. The coils in generators 32 and 64 may be configured to sense and generate signals indicative of the amplitudes of the components of these magnetic fields. Processor 36 receives and processes these signals in order to determine the pressure of the distal tip against the tissue and the position coordinates of the distal tip within the heart.

Although the operation of sensor 62 and field generator 64 in sensing pressure is described above in the context of catheter-based ablation, the principles of the present invention may similarly be applied in other therapeutic and diagnostic applications that use invasive probes, both in the heart and in other organs of the body. As one example, the devices and techniques for position and pressure sensing that are implemented in system 20 may be applied, mutatis mutandis, in guiding and controlling the use of a catheter insertion sheath. If the position of the sheath is not properly controlled and excessive force is used in its insertion, the sheath may perforate the heart wall or vascular tissue. This eventuality can be avoided by sensing the position of and pressure on the distal tip of the sheath. In this regard, the term "distal tip" as used herein should be understood to include any sort of structure at the distal end of a probe that may be bent and/or displaced relative to the main body of the probe.

It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A medical probe, comprising:
   a flexible insertion tube, having a distal end for insertion into a body cavity of a patient;
   a distal tip, which is disposed distal to the distal end of the flexible insertion tube and is configured to be brought into contact with tissue in the body cavity;
   a resilient member, which couples the distal tip to the distal end of the flexible insertion tube and is configured to deform in response to pressure exerted on the distal tip when the distal tip engages the tissue; and
   a position sensor within the medical probe for sensing a position of the distal tip relative to the distal end of the flexible insertion tube, which changes in response to deformation of the resilient member,
   wherein the position sensor is configured to generate a signal indicative of the position of the distal tip responsively to a magnetic field that is generated in a vicinity of the distal tip,
   wherein the position sensor is disposed in the distal end of the flexible insertion tube, and wherein the medical probe comprises a magnetic field generator within the distal tip for generating the magnetic field.

2. The medical probe according to claim 1, wherein the position sensor is further configured to generate a signal indicative of an axial displacement and an orientation of the distal tip relative to the distal end of the insertion tube.

3. The medical probe according to claim 1, wherein the position sensor and the magnetic field generator comprise coils.

4. The medical probe according to claim 1, wherein the resilient member comprises a spring.

5. The medical probe according to claim 1, wherein the position sensor is further configured to generate a signal, responsively to the deformation, which is indicative of the pressure exerted on the distal tip.

6. The medical probe according to claim 1, wherein the distal tip comprises an electrode, which is configured to make electrical contact with the tissue.

7. The medical probe according to claim 6, wherein the electrode is coupled to apply electrical energy to the tissue so as to ablate a region of the tissue.

8. Apparatus for performing a medical procedure inside a body of a patient, the apparatus comprising:
   a first magnetic field generator, for disposition outside the body of the patient, for generating a first magnetic field within the body;
   a probe, which comprises:
      an insertion tube having a distal end for insertion into the body of a patient;

a second magnetic field generator within the distal end of the insertion tube for generating a second magnetic field;

a distal tip, which is flexibly coupled distal to the end of the insertion tube; and a sensor, which is disposed within the distal tip and is configured to generate first and second signals responsively to the first and second magnetic fields, respectively; and a processor, which is coupled to receive and process the first signal so as to determine coordinates of the distal tip within the body and to receive and process the second signal so as to detect changes in a position of the distal tip relative to the distal end of the insertion tube.

9. The apparatus according to claim 8, wherein the changes in the position of the distal tip detected by the processor comprise axial displacement of the distal tip and deflection of the distal tip relative to the distal end of the insertion tube.

10. The apparatus according to claim 8, wherein the distal tip is rigid, and wherein the probe comprises a resilient member, which couples the distal tip to the distal end of the insertion tube.

11. The apparatus according to claim 10, wherein the resilient member is configured to deform in response to pressure exerted on the distal tip when the distal tip engages tissue inside the body, and wherein the changes in the position of the distal tip are indicative of deformation of the resilient member.

12. The apparatus according to claim 11, wherein the processor is configured to generate, responsively to the deformation, an output that is indicative of the pressure exerted on the distal tip.

13. The apparatus according to claim 8, wherein the sensor and the second magnetic field generator comprise coils.

14. The apparatus according to claim 10, wherein the resilient member comprises a spring.

15. The apparatus according to claim 8, wherein the distal tip comprises an electrode, which is configured to make electrical contact with the tissue.

16. The apparatus according to claim 15, wherein the electrode is coupled to apply electrical energy to the tissue so as to ablate a region of the tissue.

17. The apparatus according to claim 8, wherein the processor is configured to generate a control input for automatically controlling motion of the probe within the body responsively to the first and second signals.

18. A method for contacting tissue in a body cavity of a patient, the method comprising:

inserting a probe into the body cavity, the probe comprising a flexible insertion tube and a distal tip, which is coupled distal to a distal end of the flexible insertion tube by a resilient member, and comprising a position sensor, which generates a signal indicative of a position of the distal tip relative to the distal end of the flexible insertion tube, which changes in response to deformation of the resilient member, wherein the position sensor is disposed in the distal tip, and wherein the probe comprises a magnetic field generator within the distal end of the flexible insertion tube for creating a magnetic field;

advancing the probe within the body cavity so that the distal tip engages and applies a pressure against the tissue, thereby causing the resilient member to deform; and processing the signal while the distal tip engages the tissue so as to provide an indication of change in the position of the distal tip relative to the distal end of the flexible insertion tube and the pressure exerted against the tissue.

19. The method according to claim 18, wherein the signal is indicative of an axial displacement and an orientation of the distal tip relative to the distal end of the flexible insertion tube.

20. The method according to claim 18, wherein the probe further comprises an electrode on the distal tip;

and wherein advancing the probe further comprises bringing the electrode on the distal tip into electrical contact with the tissue.

21. The method according to claim 20, and further comprising applying electrical energy to the electrode so as to ablate a region of the tissue that is engaged by the distal tip.

22. The method according to claim 21, wherein applying the electrical energy comprises controlling application of the electrical energy responsively to the indication of the pressure, so that the electrical energy is applied to the electrode when the pressure is within a desired range.

23. The method according to claim 18, wherein the magnetic field generated by the magnetic field generator in the distal end of the flexible insertion tube is a first magnetic field, and the signal generated by the position sensor responsively to the first magnetic field is a first signal, and wherein the method comprises:

creating a second magnetic field in a frame of reference that is fixed outside the body cavity; and processing a second signal generated by the position sensor in response to the second magnetic field so as to determine coordinates of the distal tip within the body cavity.

24. Apparatus for performing a medical procedure inside a body of a patient, the apparatus comprising:

a probe, which comprises:

an insertion tube having a distal end for insertion into the body of a patient;

a distal tip, which is flexibly coupled distal to the distal end of the insertion tube;

a magnetic field generator, which is disposed within the distal tip and is configured to generate a magnetic field; and a first sensor within the distal end of the insertion tube for generating a first signal in response to the magnetic field; and a second sensor, for disposition outside the body of the patient, for generating a second signal in response to the magnetic field;

a processor, which is coupled to receive and process the second signal so as to determine coordinates of the distal tip within the body and to receive and process the first signal so as to detect changes in a position of the distal tip relative to the distal end of the insertion tube.

25. A medical probe, comprising:

a flexible insertion tube, having a distal end for insertion into a body cavity of a patient;

a distal tip, which is disposed distal to the distal end of the flexible insertion tube and is configured to be brought into contact with tissue in the body cavity;

a resilient member, which couples the distal tip to the distal end of the flexible insertion tube and is configured to deform in response to pressure exerted on the distal tip when the distal tip engages the tissue; and a position sensor within the medical probe for sensing a position of the distal tip relative to the distal end of the flexible insertion tube, which changes in response to deformation of the resilient member, wherein the position sensor is configured to generate a signal indicative of the position of the distal tip responsively to a magnetic field that is generated in a vicinity of the distal end, wherein the position sensor is disposed in the distal tip of the flexible insertion tube, and wherein the medical probe comprises a magnetic field generator within the distal end for generating the magnetic field.

26. The medical probe according to claim 25, wherein the position sensor is further configured to generate a signal indicative of an axial displacement and an orientation of the distal tip relative to the distal end of the flexible insertion tube.

27. The medical probe according to claim 25, wherein the position sensor and the magnetic field generator comprise coils.

28. The medical probe according to claim 25, wherein the resilient member comprises a spring.

29. The medical probe according to claim 25, wherein the position sensor is further configured to generate a signal, responsively to the deformation, which is indicative of the pressure exerted on the distal tip.

30. The medical probe according to claim 25, wherein the distal tip comprises an electrode, which is configured to make electrical contact with the tissue.

31. The medical probe according to claim 30, wherein the electrode is coupled to apply electrical energy to the tissue so as to ablate a region of the tissue.

32. A method for contacting tissue in a body cavity of a patient, the method comprising:
inserting a probe into the body cavity, the probe comprising a flexible insertion tube and a distal tip, which is coupled distal to a distal end of the flexible insertion tube by a resilient member, and comprising a position sensor, which generates a signal indicative of a position of the distal tip relative to the distal end of the flexible insertion tube, which changes in response to deformation of the resilient member, wherein the position sensor is disposed in the distal end, and wherein the probe comprises a magnetic field generator within the distal tip of the flexible insertion tube for creating a magnetic field;
advancing the probe within the body cavity so that the distal tip engages and applies a pressure against the tissue, thereby causing the resilient member to deform; and
processing the signal while the distal tip engages the tissue so as to provide an indication of change in the position of the distal tip relative to the distal end of the flexible insertion tube and the pressure exerted against the tissue.

33. The method according to claim 32, wherein the signal is indicative of an axial displacement and an orientation of the distal tip relative to the distal end of the flexible insertion tube.

34. The method according to claim 32, wherein the probe further comprises an electrode on the distal tip; and wherein advancing the probe comprises bringing the electrode on the distal tip into electrical contact with the tissue.

35. The method according to claim 34, and further comprising applying electrical energy to the electrode so as to ablate a region of the tissue that is engaged by the distal tip.

36. The method according to claim 35, wherein applying the electrical energy comprises controlling application of the electrical energy responsively to the indication of the pressure, so that the electrical energy is applied to the electrode when the pressure is within a desired range.

37. The method according to claim 32, wherein the magnetic field generated by the magnetic field generator in the distal tip of the flexible insertion tube is a first magnetic field, and the signal generated by the position sensor responsively to the first magnetic field is a first signal, and wherein the method comprises:
creating a second magnetic field in a frame of reference that is fixed outside the body cavity; and
processing a second signal generated by the position sensor in response to the second magnetic field so as to determine coordinates of the distal tip within the body cavity.

\* \* \* \* \*